United States Patent
Mullins et al.

(10) Patent No.: US 6,850,317 B2
(45) Date of Patent: Feb. 1, 2005

(54) APPARATUS AND METHODS FOR DETERMINING VELOCITY OF OIL IN A FLOW STREAM

(75) Inventors: Oliver C. Mullins, Ridgefield, CT (US); Donald Charles McKeon, Paris (FR); Felix Chen, Newtown, CT (US); Xu Wu, Beijing (CN); Elizabeth B. Dussan V, Ridgefield, CT (US); Henning Groenzin, Lexington, MA (US); Clelia Canuel, Paris (FR)

(73) Assignee: Schlumberger Technology Corporation, Ridgefield, CT (US)

( * ) Notice: Subject to any disclaimer, the term of this patent is extended or adjusted under 35 U.S.C. 154(b) by 80 days.

(21) Appl. No.: 10/055,070

(22) Filed: Jan. 23, 2002

(65) Prior Publication Data

US 2003/0029995 A1 Feb. 13, 2003

Related U.S. Application Data

(60) Provisional application No. 60/263,531, filed on Jan. 23, 2001.

(51) Int. Cl.$^7$ ............................................. G01N 33/28
(52) U.S. Cl. ........................................................ 356/70
(58) Field of Search ........................... 356/318, 70, 73, 356/300, 326, 337, 338, 342, 343, 402, 432

(56) References Cited

U.S. PATENT DOCUMENTS

| | | | |
|---|---|---|---|
| 5,831,743 A | | 11/1998 | Ramos et al. ............... 356/445 |
| 6,016,191 A | * | 1/2000 | Ramos et al. ................. 356/70 |
| 6,023,340 A | | 2/2000 | Wu et al. .................... 356/432 |
| 6,075,611 A | | 6/2000 | Dussan V. et al. .......... 356/432 |
| 6,472,205 B1 | * | 10/2002 | Tsien et al. ................. 435/325 |

OTHER PUBLICATIONS

Groenzin, H. et al. "Resonant Fluorescence Quenching of Aromatic Hydrocarbons by Carbon Disulfide". Journal of Physical Chemistry A, vol. 103, No. 11 (1999), pp. 1504–1508.

Mullins, O. C. "Structures and Dynamics of Asphaltenes". Plenum Press (1998), Chapter II.

Patel, V. et al. "Evaluation of New Wells". Well Evaluation Conf. (1997) , Chapter 5.

Wang, X et al. "Fluorescence Lifetime Studies of Crude Oils". Applied Spectroscopy, vol. 48, No. 8, (1994), pp. 977–984.

Zhu, Y. et al. "Temperature Dependence of Fluorescence of Crude Oils and Related Compounds". Energy and Fuels, vol. 6, No. 5, (1992), pp. 545–552.

* cited by examiner

Primary Examiner—Michael P. Stafira
(74) Attorney, Agent, or Firm—David P. Gordon; William B. Batzer; John J. Ryberg

(57) ABSTRACT

Apparatus and methods for measuring oil flow velocity in a well are provided which utilize fluorescence quenching. A marker which quenches the natural fluorescence of crude oil is chosen and injected into the oil flow at a first location. At a second location, the oil flow is subjected to light at a wavelength which will cause oil to naturally fluoresce. The fluorescence signal is detected at the second location by a sensing probe. The time that it takes for the quenching marker to move from the first location to the second location is measured by sensing a decrease in fluorescence due to the quencher. Fluid velocity is determined by dividing the distance between the marker-ejection point and the optical probe position by the time it took the marker to move that distance.

21 Claims, 10 Drawing Sheets

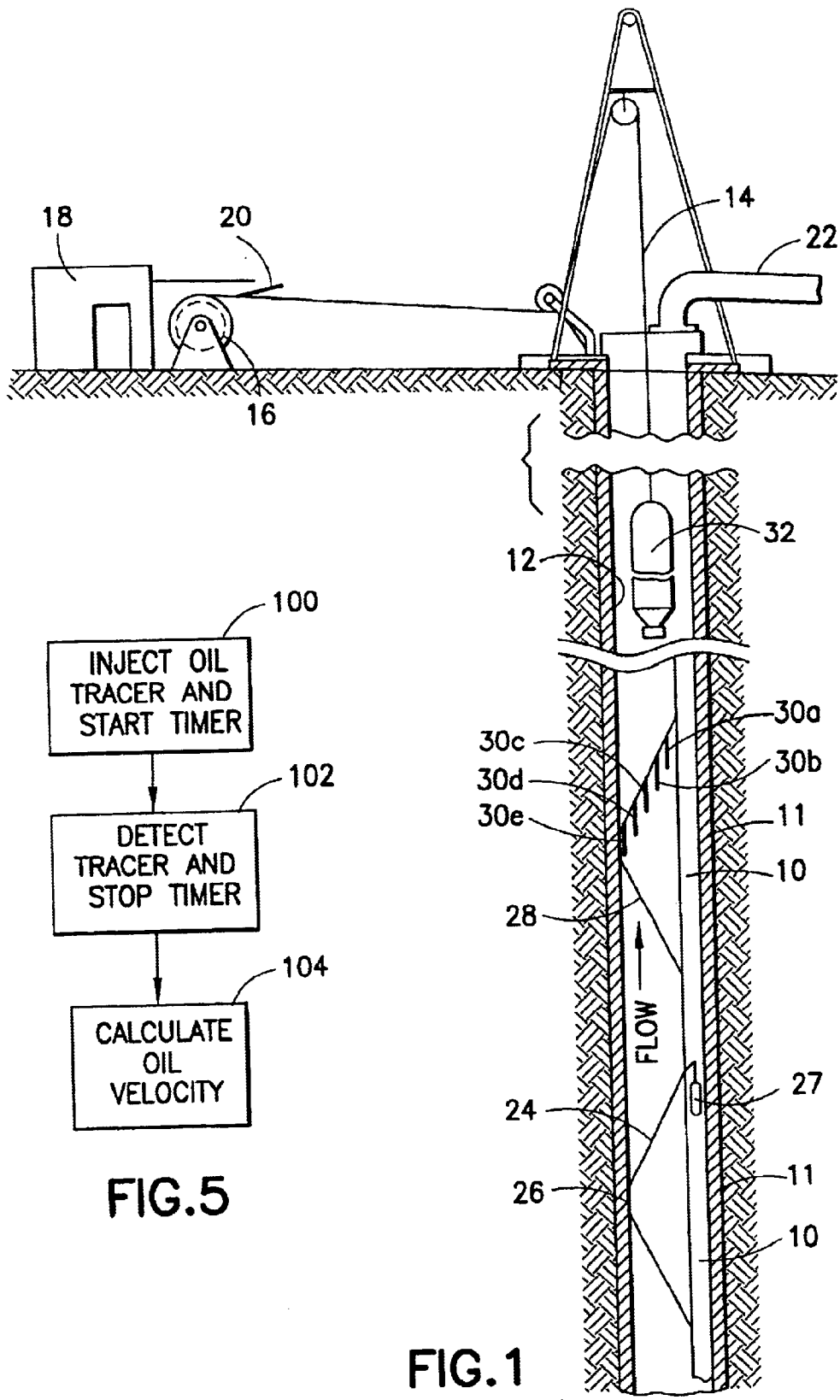

APPARATUS AND METHODS FOR DETERMINING VELOCITY OF OIL IN A FLOW STREAM

This application claims priority from provisional patent application Ser. No. 60/263,531 filed Jan. 23, 2001.

This application is related to co-owned U.S. Pat. No. 5,831,743 entitled "Optical Probes", U.S. Pat. No. 6,016,191 entitled "Apparatus and Tool Using Tracers and Single Point Optical Probes for Measuring Characteristics of Fluid Flow in a Hydrocarbon Well and Methods of Processing Resulting Signals", U.S. Pat. No. 6,023,340 entitled "Single Point Optical Probe for Measuring Three-Phase Characteristics of Fluid Flow in a Hydrocarbon Well", and U.S. Pat. No. 6,075,611 entitled "Methods and Apparatus Utilizing a Derivative of a Fluorescence Signal for Measuring the Characteristics of a Multiphase Fluid Flow in a Hydrocarbon Well", all of which are hereby incorporated by reference herein in their entireties.

This application is also related to co-owned, concurrently filed U.S. Ser. No. 10/055,654, now issued as U.S. Pat. No. 6,704,109 and entitled "Downhole Fluorescence Detection Apparatus" and U.S. Ser. No. 10/055,420 entitled "Optical Probes and Probe Systems for Monitoring Fluid Flow in a Well", both of which are hereby incorporated by reference herein in their entireties.

BACKGROUND OF THE INVENTION

1. Field of the Invention

The present invention relates to methods and apparatus for determining the velocity of oil flowing in a well. The present invention more particularly relates to the use of optical fluorescence techniques for marking oil flowing in a well.

2. State of the Art

After drilling is completed, in many hydrocarbon wells the borehole is lined with a casing. In order to extract hydrocarbon fluids (oil and gas) from the formation surrounding the borehole, holes are made in the wall of the casing. The location of the holes is usually determined by reference to information acquired about the formation during the drilling operation, and/or after drilling with the aid of logging instruments before the casing is installed.

Various methods are used to urge the fluid out of the formation, into the well, and up to the surface. In most cases, the fluid traveling to the surface is a mixture of two or three fluid components (phases): oil (liquid hydrocarbon), hydrocarbon gas, and water (or brine). The fluid is collected at the surface and is handled in different ways, depending on the relative proportion of each phase. For example, if the fluid contains a relatively small amount of gas, the gas may be burned at the well site since it is not economically practical to process small amounts of gas. If the fluid contains relatively large amounts of water, it may be economically impractical to continue production operations at the site. In fact, even while the well is producing petroleum products, the disposal of water produced from the well is very costly. In general, the different phases of the well fluid enter the well from different locations, and a high water content can be the result of improperly located perforations in the casing. If it is possible to determine where water is entering the well, perforations in the casing can be plugged and the proportional amount of water in the fluid reduced.

The relative volumetric flow rates (flow rate fractions) of the oil, gas, and water through the well is known in the art as the "cut". The "holdup" is a measure of relative proportions of each phase in a selected volume of fluid in the well; i.e., the volume fraction. The cut and holdup are not in general the same, because the different phases may be, and are in general, flowing at different average speeds. In addition, both the volumetric flow rate and the volume fraction will vary over time and vary at different depths in the well.

Various methods and devices have been used for many years to estimate the volumetric flow rate and the holdup of each phase at different depths in a well over time. Most of the methods of the prior art measure volumetric flow rate or holdup averaged over the cross-sectional area of the wellbore. The principal devices for measuring flow rates employ propellers or turbines which are assumed to measure the average volumetric flow rate of the entire fluid mixture. However, propellers and turbines are typically ineffective in providing even their limited quantitative measurement when the well is not substantially vertical (i.e., when the well deviates more than five degrees from vertical). Other devices of the art measure differential pressure to determine the average density of the flowing mixture. These devices lose their accuracy when fluid flow rate is high or the well is substantially inclined. Still other methods and devices for measuring holdup include the use of electrical plates to measure capacitance of the fluid and make a determination of the fluid content based on variations in capacitance. Similar systems measure resistivity or measure dielectric constant in the presence of RF radiation.

Recent devices derive the wellbore cross-sectional averaged volumetric flow rate and holdup from a number of local measurements made within the wellbore. The accuracy of these averaged volumetric flow rate and holdup determinations depends on the accuracy of each local sensor (probe), the deployment of a sufficient number of probes, and, in the case of non-vertical wells, knowledge of multiphase flow in the inclined pipe. To date, the local sensors which have been used have been mostly electrical sensors which respond to the resistivity of the fluids in the wellbore. However, electrical probes can only measure the holdup and volumetric flow rates of the dispersed phase (e.g., the oil holdup in an oil-water system which is more than about sixty-five percent water).

For continuous phase velocity (liquid system), the method presently considered of choice is to use tracers (sometimes referred to as markers). Continuous phase velocities are particularly important in the high tier market of horizontal wells. A tracer is injected into or created in the flow stream and its arrival downstream is recorded. Typically, the tracer is required to travel approximately ten pipe diameters (or more) to provide a sufficiently well developed flow.

There are at least three well known tracers methods: radioactive tracers, oxygen activation, and a gadolinium tracer. The radioactive tracer consists of a fluid with a relatively short-half life (hours or a few days). A gamma-ray detector is used to measure the velocity via the time-of-flight technique (distance/time). This technique has the disadvantage of requiring the storage, handling, and ejection of a radioactive material.

With oxygen activation, a neutron generator is used to convert stable oxygen into a radioactive isotope of nitrogen. A gamma-ray detector is used to detect the time that the activated material reaches the detector. There is no direct handling of radioactive materials, but the technique has problems with slow velocities and the need for the source-to-detector spacing of ten diameters.

The gadolinium tracer may be used in either a water-soluble or an oil-soluble compound to monitor the respective phase velocities. Because of its extremely high thermal neutron capture cross section, the Gd tracer causes a change in the absorption decay rate of the host phase. A thermal-decay time tool (like the RST-A tool) is used to detect this change as the Gd-doped fluid passes the tool's gamma-ray detectors. This technique requires use of a thermal-decay time tool, thus increasing the cost and complexity of phase velocity acquisition. (Other isotopes such as boron can be used instead of Gadolinium, but the signal-to-noise ratio is much worse).

A fourth tracer technique is disclosed in previously incorporated U.S. Pat. No. 6,016,191 to Ramos et al. According to the '191 patent, a fluorescent tracer is injected at a first location into the flowing fluid, light having a wavelength which causes the fluorescent tracer to fluoresce is introduced into the fluid at a second location, and a detector at the second location which detects light at the fluorescing wavelength is used to determine when the tracer is present. The distance between the locations, and the time it takes from injection of the fluorescent tracer until detection by the detector provides an average fluid velocity. According to the '191 patent, an oil soluble tracer is utilized when oil constitutes the continuous phase of the fluid, and a water soluble tracer is used when water constitutes the continuous phase of the fluid.

Previously incorporated U.S. Pat. No. 6,023,340 to Wu et al. and U.S. Pat. No. 6,075,611 to Dussan et al. also utilize an optical system which measures fluorescence in order to measure oil velocity; albeit without the aid of a tracer. In particular, the '611 patent suggests that light can be injected into a multiphase fluid at a first wavelength which will cause oil to naturally fluoresce at a second wavelength, and that detection of the fluorescence signal over time (and processing of the derivative signal thereof) can be used to obtain information regarding oil drop velocity, flow rate and holdup.

While the techniques described in the previously incorporated patents represent large steps forward in the art, and are useful in most circumstances, there exists at least one particular circumstance when a fluorescing marker or the natural fluorescence of the oil cannot be easily utilized to measure oil velocity. In particular, in a single phase flow of heavy oils, the natural fluorescence cannot be utilized because oil droplets are not distinct. Likewise, the fluorescing marker cannot be easily utilized because the heavy oil is optically opaque, and the fluorescent tracer would have to be present at unacceptably high concentrations to compete for injected photons. In addition, the natural fluorescence of heavy crudes can interfere with the fluorescence measurements of the marker.

SUMMARY OF THE INVENTION

It is therefore an object of the invention to provide apparatus and methods for measuring the velocity of oil flowing in a well.

It is another object of the invention to provide apparatus and methods for determining oil flow velocity using optical techniques.

It is a further object of the invention to provide mechanisms for measuring oil flow velocity in a well which utilize existing tools of the art.

In accord with the objects of the invention, apparatus and methods for measuring oil flow velocity in a well are provided which utilize fluorescence quenching. In particular, a marker which quenches the natural fluorescence of crude oil is chosen and injected into the oil flow at a first location.

At a second location, the oil flow is subjected to light at a wavelength which will cause oil to naturally fluoresce. The fluorescence signal is detected at the second location by a sensing probe. The time that it takes for the quenching marker to move from the first location to the second location is measured by sensing a decrease in fluorescence due to the quencher. Fluid velocity is determined by dividing the distance between the marker-ejection point and the optical probe position by the time it took the marker to move that distance.

Fluorescence quenching may be accomplished in three fundamental ways: the tracer can absorb the source light making it unavailable to excite fluorescence in the oil; the tracer can absorb fluorescing light thereby reducing the amount of light at the fluorescence wavelengths detected; and the tracer may quench fluorescence of the crude oil by deactivating electronically excited states of the crude oil aromatic molecules which are primarily responsible for crude oil fluorescence. Recognizing these different mechanisms for quenching, various fluorescence quenchers or combinations thereof may be utilized. The quencher is preferably a liquid, and may take the form of a solute dissolved in a solvent. The solute and the solvent may be chosen such that they quench fluorescence in different manners.

Additional objects and advantages of the invention will become apparent to those skilled in the art upon reference to the detailed description taken in conjunction with the provided figures.

BRIEF DESCRIPTION OF THE DRAWINGS

FIG. 1 is a schematic diagram of a production logging tool incorporating a tracer injector and detector apparatus according to the invention in an oil well and coupled to associated surface equipment;

FIG. 5 is a schematic block diagram of signal processing methods according to the invention for determining oil velocity.

DETAILED DESCRIPTION OF THE PREFERRED EMBODIMENTS

Figure 2A:
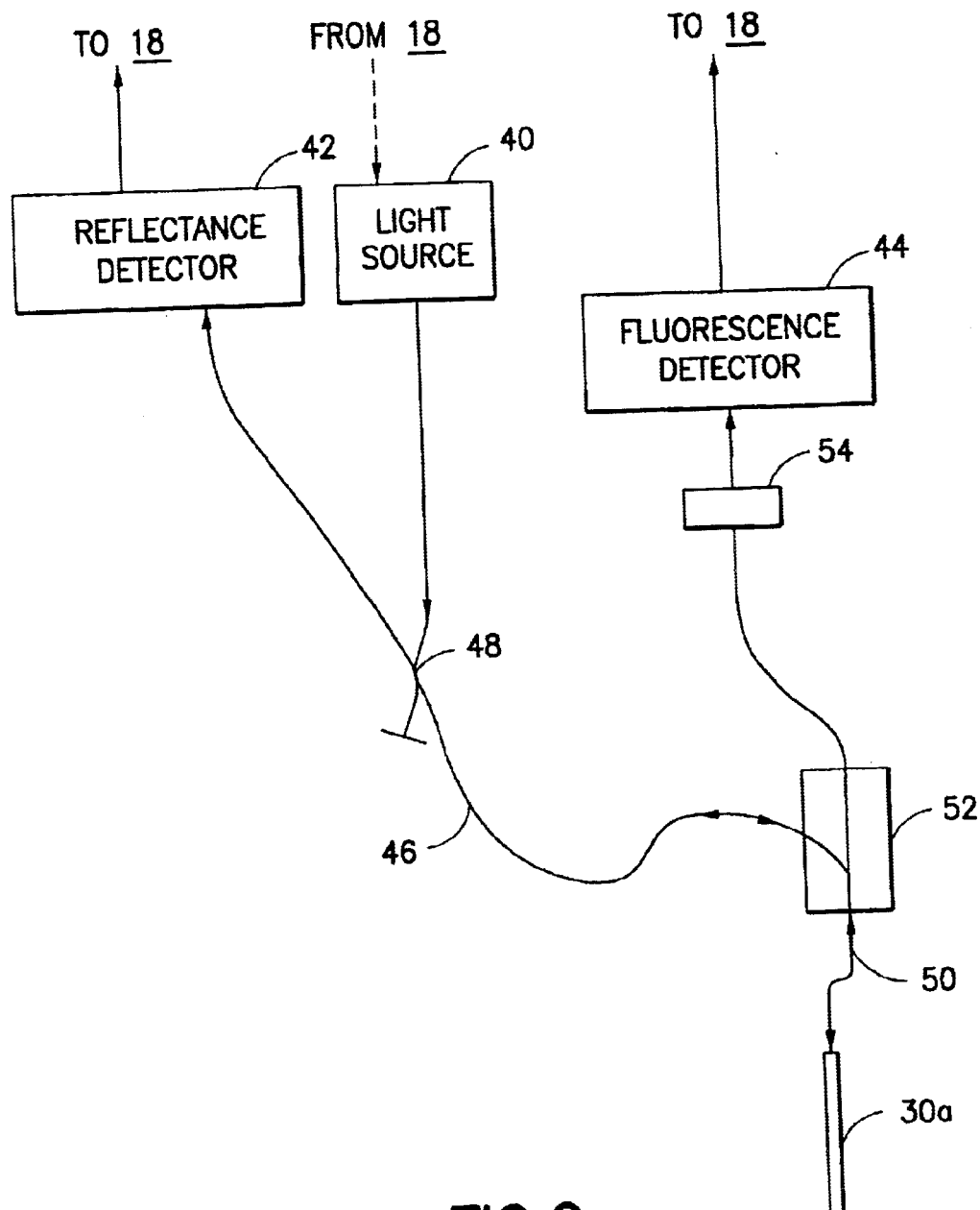
FIG. 2a is a simplified schematic diagram of a first embodiment of the coupling of a light source and detectors to an optical probe according to the invention.

For purposes of illustration, the invention will be described primarily with reference to a production logging tool. However, at the outset, it should be appreciated by those skilled in the art that the invention can be implemented as a permanent installation in a producing well.

Referring now to FIG. 1, a production logging tool 10 is suspended in a well 12 by means of a cable 14 which is coupled to a winch 16 for raising and lowering the tool 10. The cable 14 includes conductors (not shown) which may be either electrical or optical, or both, for communicating with data processing equipment 18 located on the surface. A cable displacement detector 20 is also provided at the surface in order to determine the depth of the tool 10 when it is lowered into the well 12. During production, fluid from the well is collected at the surface and conducted by a duct 22 to a storage or refining facility (not shown).

The tool 10, according to the preferred embodiment of the invention, generally includes an injection tube 24 which is coupled to a source of fluorescence quenchers (not shown) via electrically operated valves (not shown) for injecting a selected amount of the quencher into the flow of fluid inside the casing 11 (which while shown in a vertical well, may also be used in a highly deviated or horizontal well). The injection tube 24 is mounted on a first spring bow 26 and is coupled to an injector 27 which is mounted inside the tool. One or more detection probes (e.g., 30a–30e) are mounted on a second spring bow 28 which is uphole (downstream) from spring bow 26. The probes 30a–30e may take any of various formats as disclosed in the previously incorporated patents and related patent applications. Also as described in the previously incorporated patents and related patent applications, the probes are coupled to a light source and a light detector by an optical fiber, a fiber coupler, and a filter. According to one embodiment of the invention, the optical source and detection equipment are located in the tool 10, e.g. in an upper electronics housing 32. According to another embodiment, optical source and detection equipment are located with the data processing equipment 18 at the surface.

Figure 4A:
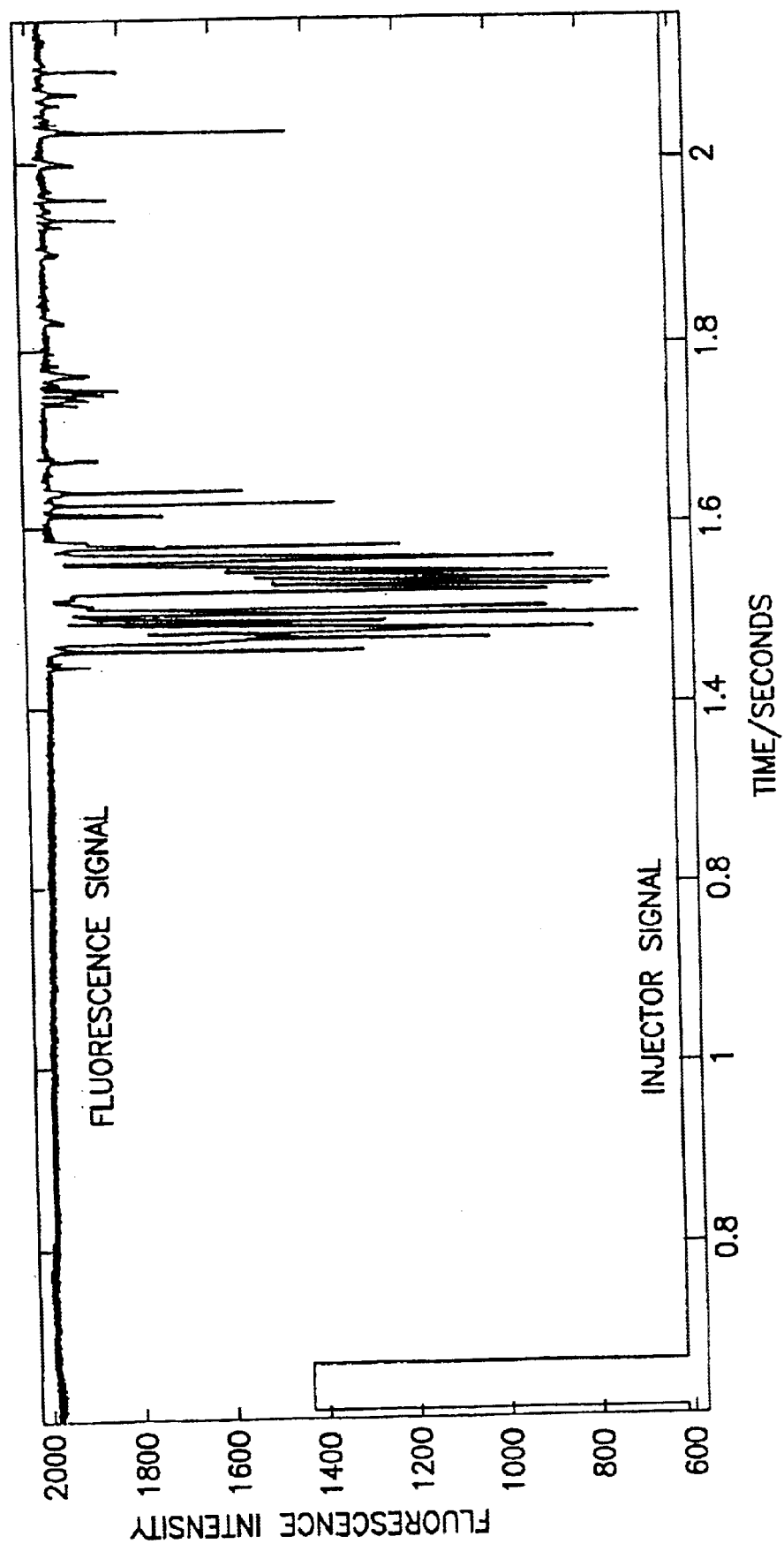
FIG. 4a is an exemplary graph of a quenched fluorescence signal from a tracer detector located a distance ten times the well diameter from the injector.

According to the invention, the injection tube and the detection probe preferably are located not too close together. In particular, the tube 24 and the probe 30 are spaced apart from each other by a distance "d" in the casing 11 which has a diameter "D". According to the invention, the distance "d" is preferably chosen relative to the diameter "D" while accounting for the turbulence of the fluid flow in order to ensure mixing of the quencher in the fluid. Often, the Reynolds number for fluid flows downhole is much greater than 2,000. If the probe and the injection tube are too close together, the signal detected when the quencher arrives at the probe will exhibit a series of (inverse) peaks corresponding to pockets of quencher which are not yet well mixed with the oil. As the probe and the injection tube are located farther apart, the quencher has more time to mix well with the fluid and the signal detected when the quencher arrives at the probe should represent a continuous distribution with a single well defined peak indicative of the average velocity of the continuous phase. For example, FIG. 4a shows a plot of the fluorescence signal detected where the distance between the injector and the probe is d=10D. The square pulse at the left of FIG. 4a indicates the time of quencher injection. The (inverse) peaks in the fluorescence signal show that the quencher is passing the probe in pockets of different concentration with the first peak indicating the maximum velocity of the quencher in turbulent flow. It is possible for a processor to estimate the average velocity from the maximum using the known well radius and the known radial location of the probe. For example, when the dispersed phase holdup is small, the continuous phase local velocity u at a radial position r can be approximated by Equation 1 where $u_{max}$ is the maximum continuous phase speed and R is the radius of the casing:

$$u = u_{max}\left(\frac{R-r}{R}\right)^{1/7} \quad (1)$$

The average continuous phase speed is given by:

$$\bar{u} = u_{max}\frac{2\pi}{\pi R^2}\int_0^R \left(\frac{R-r}{R}\right)^{1/7} r\,dr \quad (2)$$

Figure 4B:
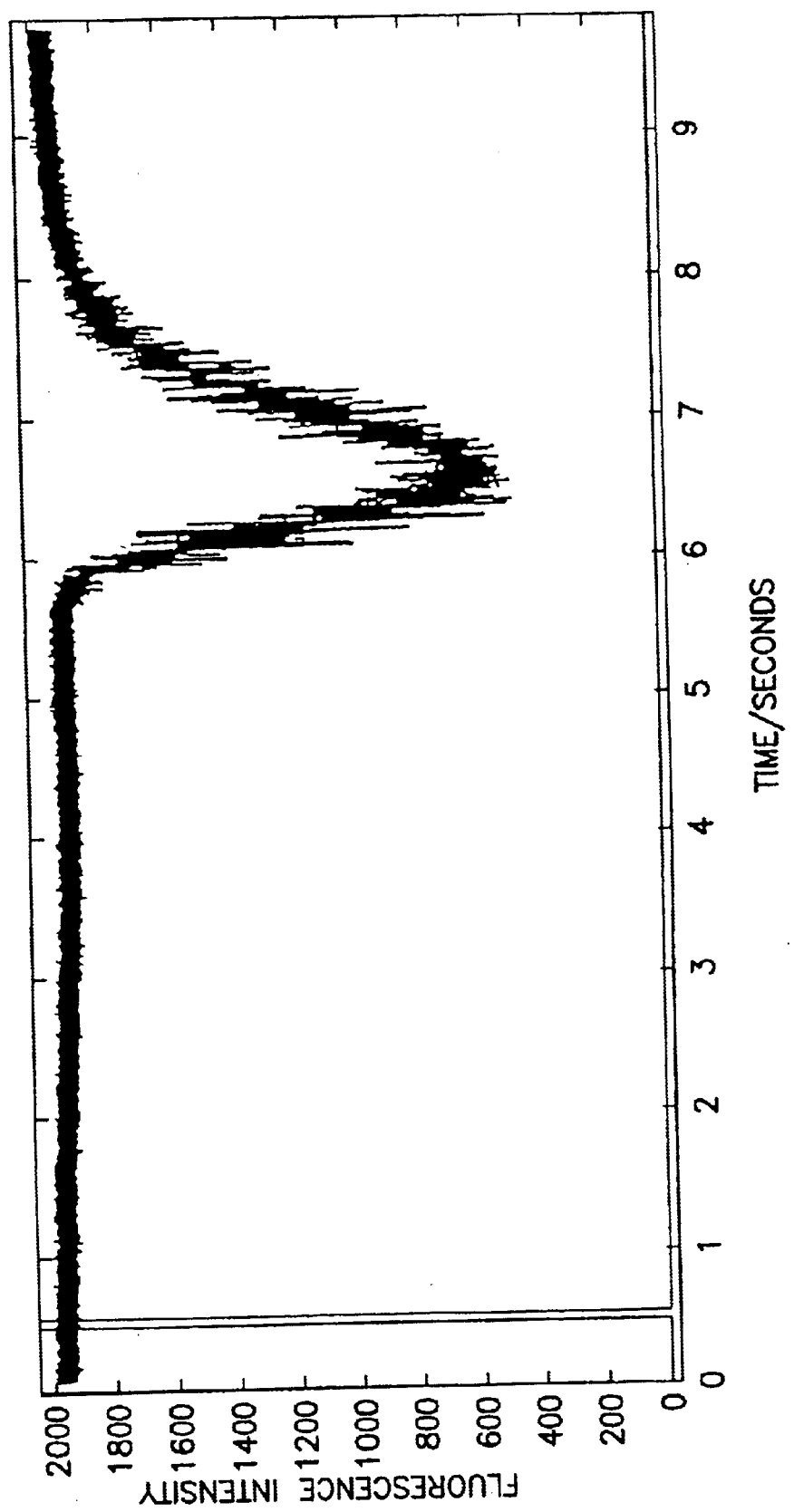
FIG. 4b is an exemplary graph of a quenched fluorescence signal from a tracer detector located a distance one hundred times the well diameter from the injector.
Figure 6A:
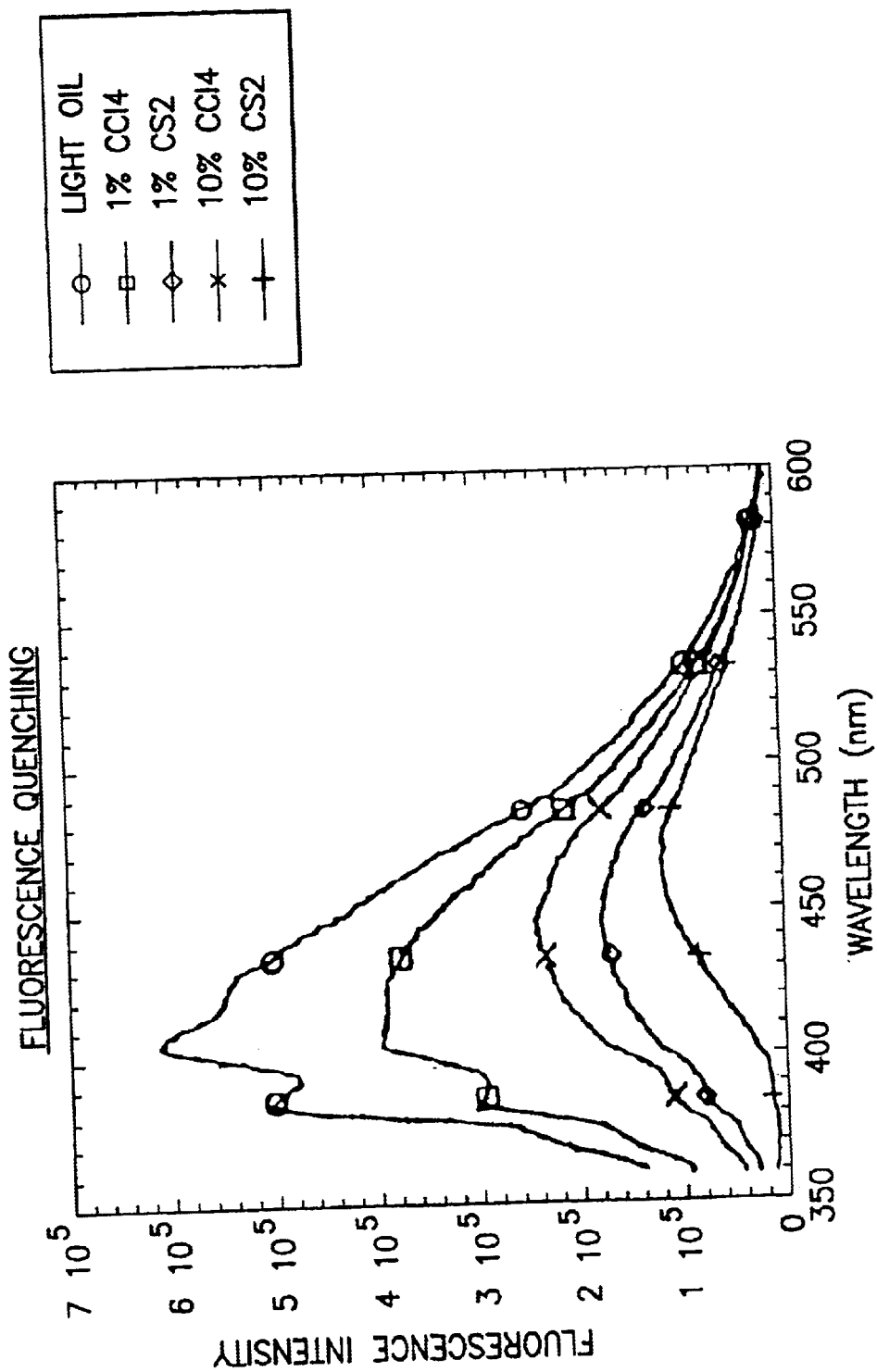
FIGS. 6a–6c are plots showing the fluorescent quenching effect at different wavelengths by different concentrations of CC14 and CS2 in light, medium, and heavy crude oils.
Figure 6B:
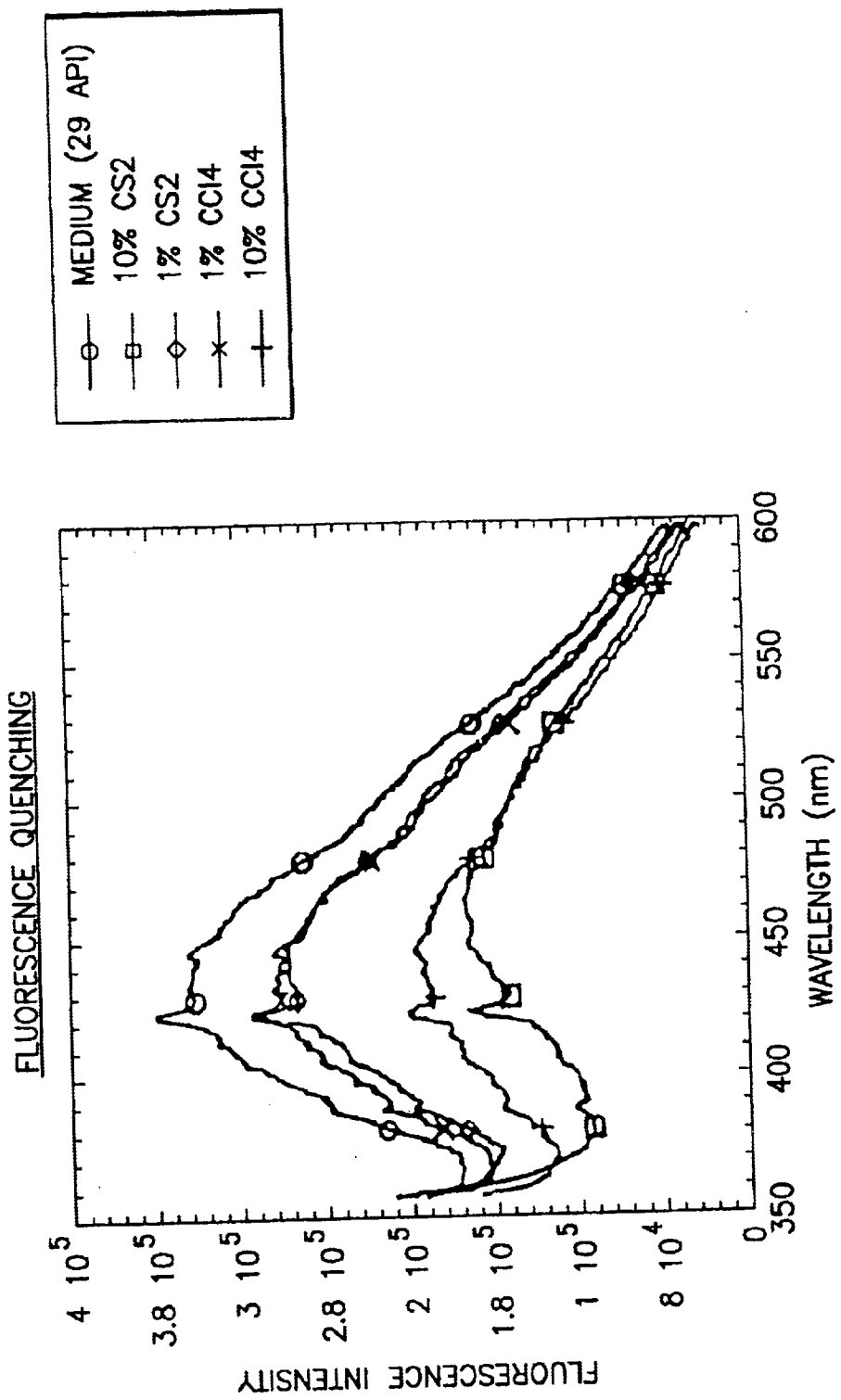
Figure 6C:
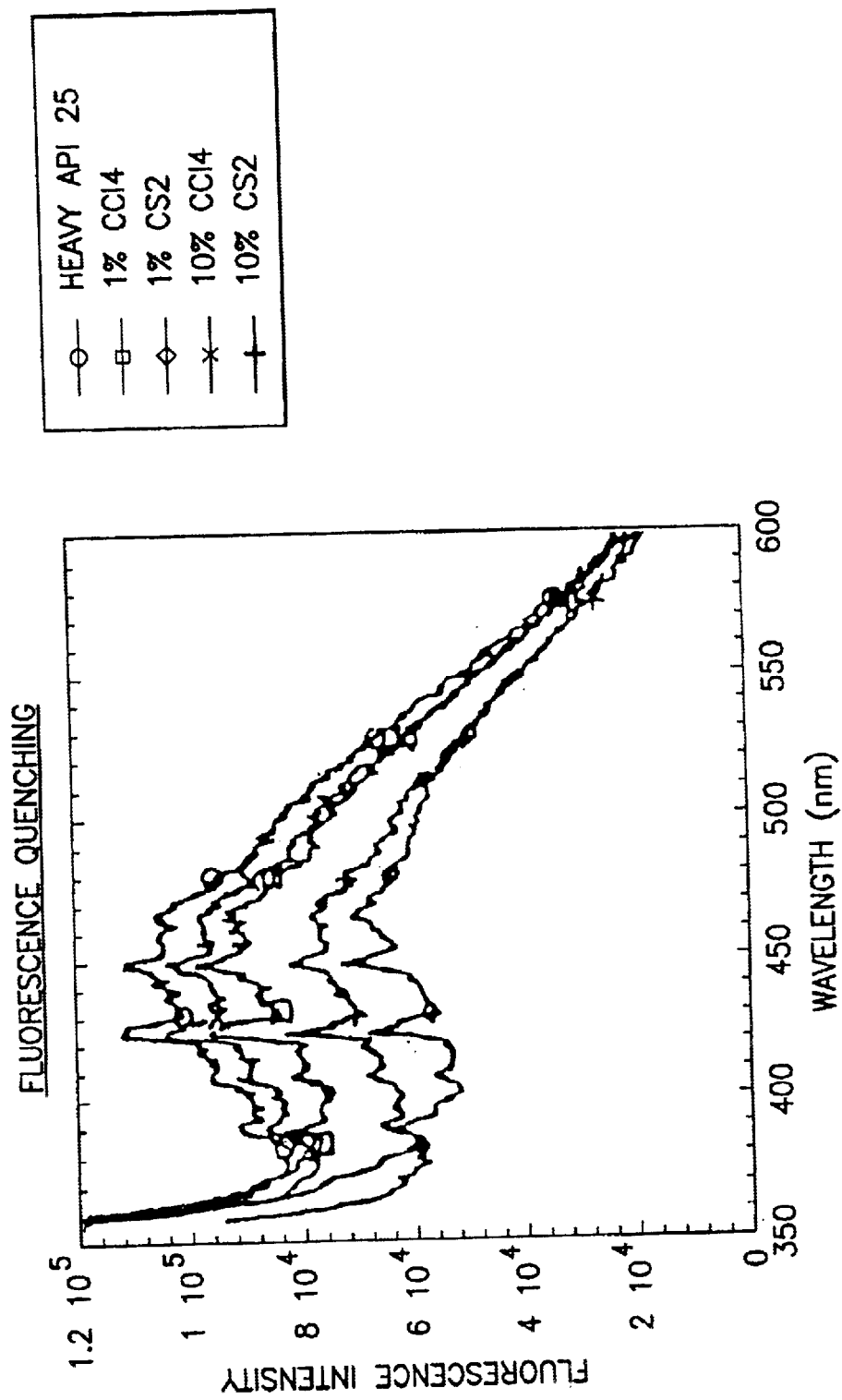

It is simpler and more accurate to move the injection tube and the probe farther apart (e.g., preferably d=22D; although d may be greater than 22D such as d=40D, or d>40D). FIG. 4b shows a plot of the fluorescence signal detected as a result of the quencher where the distance between the injector and the probe is d=100D. The square pulse at the left of FIG. 4b indicates the time of tracer injection. The inverse peaks in the fluorescence signal show that the quencher is passing the probe in pockets of different concentration. However, the concentrations are relatively continuously increasing to a recognizable peak concentration (from which an average velocity can be determined) and then relatively continuously decreasing to a level of no concentration of quencher.

Further, if desired, quencher uniformity across the fluid flow may be expedited by injecting the dye in a manner perpendicular to the fluid flow. In this manner, the quencher will not carry an initial velocity.

Turning now to FIG. 2a, in order to detect the fluorescence signal, each optical probe, e.g. 30a, is optically coupled to a respective light source 40, reflectance detector 42, and fluorescence detector 44. According to a first embodiment, the light source 40 and reflectance detector 42 are optically coupled to a first fiber optic 46 by way of a 1:1 directional coupler (fiber beam splitter) 48. The fluorescence detector 44 and the fiber optic 46 are optically coupled to a second fiber optic 50 by way of a wavelength division multiplexer 52. The second fiber optic 50 is optically coupled to the probe 30a. An optical filter 54 is optionally placed in the optical path between the multiplexer 52 and the fluorescence detector 44. The arrangement of source and detectors in this embodiment is designed to operate downhole in the logging tool. Accordingly, according to one embodiment of the invention the light source is a laser diode such as a Honeywell HFE4050 which operates correctly at temperatures up to 100° C. (although other laser diodes or non-laser light sources such as high brightness LEDs can be utilized). The laser diode emits red light in the 680–690 nm range. At this wavelength, oil will fluoresce at a wavelength in the range of 700–850 nm or longer. A suitable multiplexer for isolating fluorescent light in this spectrum is the Mux-optic MX.125 series from ATI Électronique. The use of a multiplexer and the arrangement of the components is aimed at minimizing attenuation of the fluorescent light entering the tip of the probe 30a and preventing source light and reflected light from reaching the fluorescence detector 44. This is important because the intensity of the fluorescent light is much lower than the intensity of the light source and the reflected light and, to start with, the intensity of the laser diode and other likely light sources is not very high. It will also be appreciated that in order to further minimize attenuation of the fluorescent light, the multiplexer 52 is located in the optical path between the probe 30a and the coupler 48. The optional filter 54 in this embodiment is only necessary if the multiplexer does not sufficiently prevent the detector 44 from seeing reflected light. The outputs of the detectors 42, 44 are provided in preprocessed form to data processing equipment 18 (FIG. 1) which is preferably located on the formation surface.

Figure 2B:
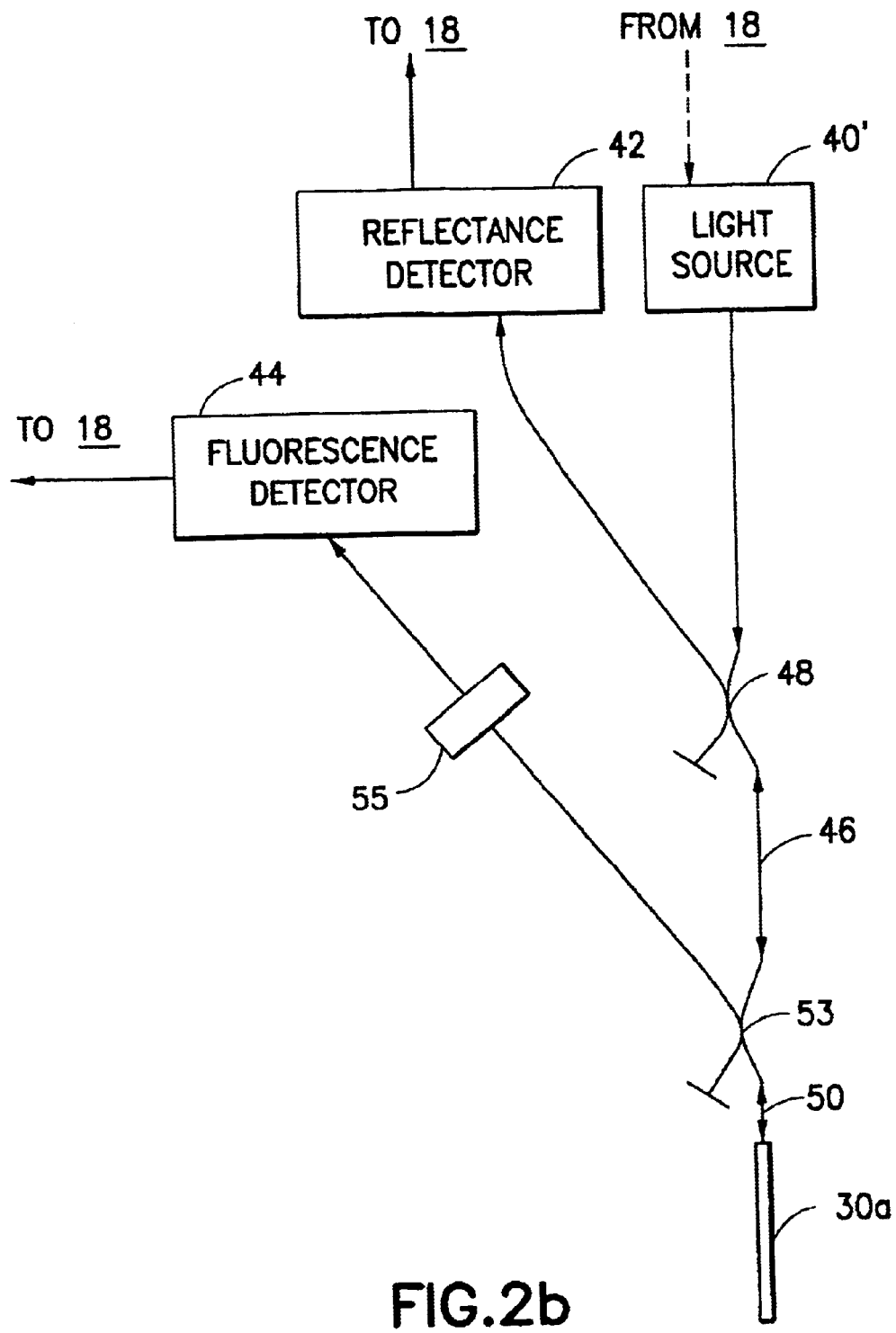
FIG. 2b is a simplified schematic diagram of a second embodiment of the coupling of a light source and detectors to an optical probe according to the invention.

An alternative arrangement of probe, source and detectors is shown in FIG. 2b. In this arrangement, there is significantly more attenuation, but the need for a multiplexer is eliminated. Thus, according to this embodiment, light source 40' and reflectance detector 42 are coupled to the first optic 46 by way of the 1:1 directional coupler (fiber beam splitter) 48. The fluorescence detector 44 and the fiber optic 46 are optically coupled to the second fiber optic 50 by way of another fiber beam splitter 53 and the second fiber optic 50 is optically coupled to the probe 30a. An optical filter 55 is placed in the optical path between the splitter 53 and the fluorescence detector 44 to prevent the detector 44 from detecting reflected light. A possible alternative to the use of the filter 55 is to provide a fiber optic with an internal grating which acts as a filter. The outputs of the detectors 42, 44 are provided in preprocessed form to data processing equipment 18 (FIG. 1) which is preferably located on the surface. In addition, according to one embodiment of the invention discussed below, the light source 40' is also controlled according to a duty cycle by the data processing equipment 18 or by downhole electronics (not shown) in housing 32 or body 24.

As mentioned above, the light source and the detectors may be located downhole in the tool or uphole with the data processing equipment. When located downhole, a compact laser diode is an appropriate light source, although other light sources high brightness LEDs may be utilized. When located uphole, however, a more powerful light source such as a higher powered laser is appropriate. Those skilled in the art will appreciate that the detectors may be fabricated from any photodetector suitable for use with the particular light source given the wavelength and intensity of the source. For example, if the light source is the laser diode mentioned above, a suitable detector would be a Honeywell HFD3022. Alternatively, if an LED with optical output of 470 nm is used, a suitable detector would be a high temperature photomultiplier such as the EMR 741N available from EMR of Princeton, N.J.

Figure 2C:
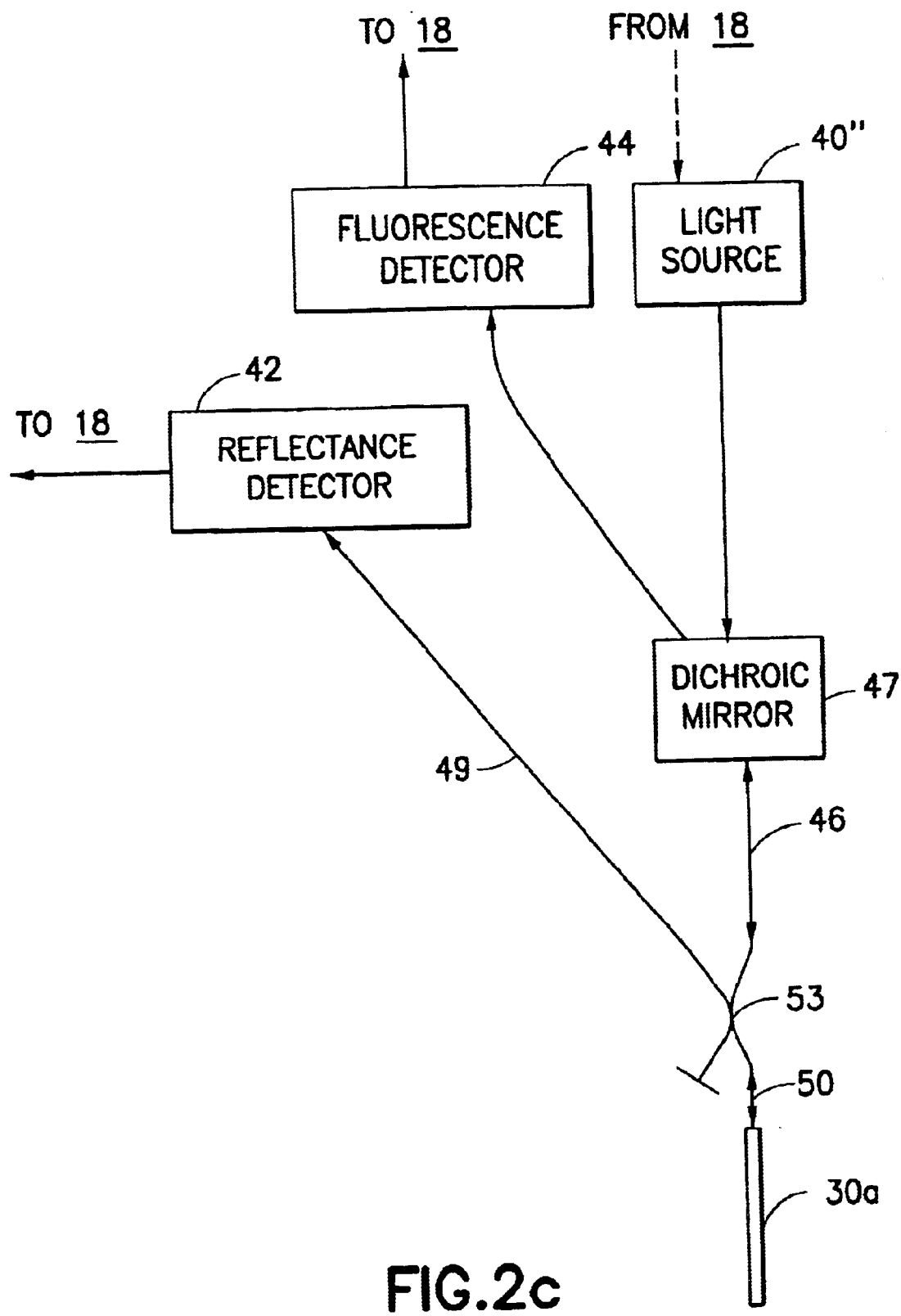
FIG. 2c is a schematic diagram of a presently preferred third embodiment of the coupling of a light source and detectors to an optical probe according to the invention.

Turning to FIG. 2c, a presently preferred arrangement of probe, source and detectors is shown. As in the other two embodiments, in the preferred embodiment of FIG. 2c, each optical probe (e.g., 30a) is optically coupled to a respective light source, reflectance detector, and fluorescence detector. According to the third preferred embodiment, the light source 40" is a light emitting diode (LED). As is discussed hereinafter with reference to FIG. 3, LED 40" and fluorescence detector 44 are coupled to the first optic 46 by way of a dichroic mirror 47. The first optic 46 and a second optic 49 (which is coupled to the reflectance detector 42) are optically coupled to another fiber optic 50 by way of a fiber beam splitter 53. The fiber optic 50 is optically coupled to the probe 30a. The beam splitter 53 is preferably arranged to pass at least ninety percent of light received from fiber optic 50 to the first fiber optic 46.

Figure 3:
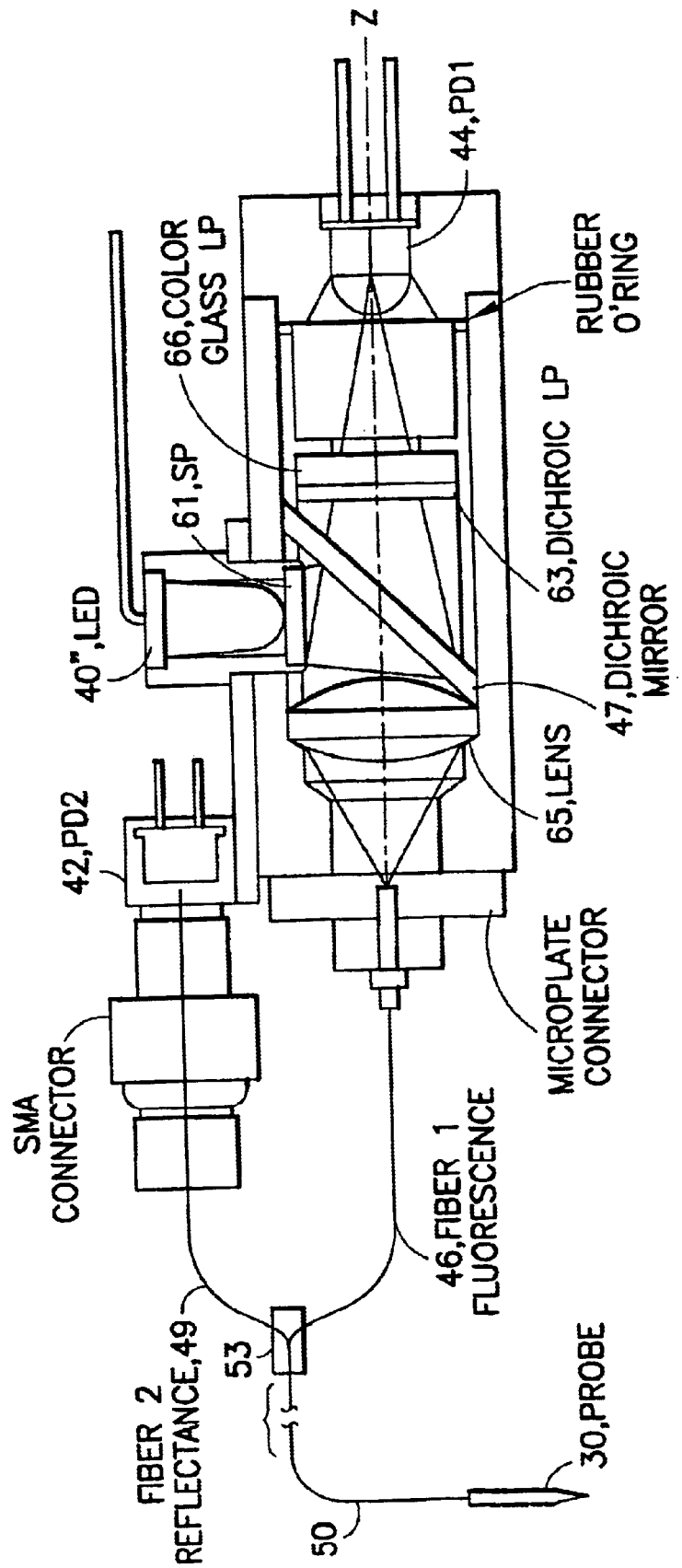
FIG. 3 is a diagram of details of the third embodiment of the coupling shown in FIG. 2c.

Additional details of the probe source and detector assembly of FIG. 2c are seen in FIG. 3 and are described in more detail in the previously incorporated concurrently filed applications. The provided assembly of optical components enables a simultaneous detection of fluorescence and reflectance from a single fiber probe. The design maximizes signal sensitivity with a low noise figure. Tests have shown its reliable performance at high temperature. The assembly includes, among other things, a light source 40", a reflectance detector 42, a fluorescence detector 44, a first optic 46, a dichroic mirror 47, a second optic 49, a third fiber optic 50, a beam splitter/coupler 53, the probe 30, a short pass filter 61, a dichroic long pass filter 63, and a lens 65. The light source 40" is a light emitting diode (LED). LEDs are not as good as lasers in terms of the coupling efficiency with fiber optics, but their energy conversion efficiency is comparable to lasers. Also, LEDs can work at considerably higher temperature than their laser counterparts. They are low cost, small, fairly narrow in bandwidth and simple to operate. LEDs are available in a broad range of wavelengths, from UV (375 nm) to near infrared, and in a variety of packaging. In the preferred embodiment, the LED is epoxy resin packaged with a light directivity (the emission half-angle) between 7 to 15 degrees, although LEDs in other packaging and with different light directivity may be used The short-pass filter 61 is an optical element that passes light below a certain wavelength (known as the filter edge) while rejecting light above that wavelength. The short-pass filter cuts off the tail emission of the source LED 40". The fluorescence of crude oils spreads over a range of wavelengths. The fluorescence is the strongest next to the excitation wavelength and decreases quickly as the wavelength moves away from it. The emission spectrum of an LED, on the other hand, exhibits a Gaussian distribution. Namely, its radiation extends to both sides of the center peak, and so will overlap with the fluorescence. Though the power intensity fades quickly, the tail of the source is still strong enough to overwhelm the usually feeble signal of fluorescence. To address this problem, the short-pass filter 61 is put in front of the LED to clean up the tail emission. The preferred short-pass filter has a steep transition in absorbance, from OD 0.1 to OD 4 in just a few tens of nanometers in wavelength. The edge of the filter (transition) is set next to the main emission of the source LED before the signal band starts. This cuts off the leakage of the tail emission effectively by four orders of magnitude (OD 4).

The dichroic mirror 47 reflects the main portion of the LED emission spectrum by ninety degrees, and the reflected light is focused with the lens 65 toward the entrance of a fiber optic 46. The reflection band of the mirror 47 is tailored according to the source wavelength; i.e. it reflects mainly the source emission but allows longer wavelength portion of the spectrum (fluorescence) coming back from the fiber optics to pass through. In this respect, it functions just like a long-pass filter (LP). Thus, both the source input and the signal paths are able to utilize the full cross-section of the fiber optics, helping achieve a high fluorescence signal level. The center of the edge of the dichroic mirror transmission (corresponding to the 50% transmission) is placed in the middle of those between the short-pass filter 61 and the long-pass filter 63.

Because the source excitation and the returning signals (reflectance and fluorescence) share the same optical path (i.e., fiber optic 50) at the probe, they have to be divided somewhere along the optical path. According to the preferred embodiment of the invention, a splitter 53 (also called a coupler, depending on which direction the light goes) is used to split the optical power from fiber 50 into two or more branches (fibers 46 and 49). Because the reflectance signal is two or three orders of magnitude stronger than the fluorescence signal, and the light directed to the reflectance detector is taken from the total, i.e., at the price of reducing the power injection and the fluorescence, in the preferred embodiment of the invention, splitter 53 is preferably arranged to provide at least ninety percent of the signal to the fluorescence detection optic 46 and at most ten percent to the reflectance detection optic 49. Details of a preferred splitter are seen in the previously incorporated concurrently filed applications.

In order to detect the very weak fluorescence signal, the reflected source light as well as the source scattering are preferably blocked out at the fluorescence detector 44. This is achieved by using the long-pass filter 63 in addition to the dichroic mirror 47 mentioned above. The long-pass filter 63 allows the transmission of wavelengths longer than the filter edge while rejecting those below it. Similar to the short-pass filter, the rejection/pass transition can occur in just several tens of nanometers from OD>4 to OD 0.1. According to the invention, the long-pass filter can be made of either a stack of dichroic layers or of color glass, or both. The spectral edges of the short-pass filter 61 and the long-pass filter 63 are preferably chosen to be as close as possible so as to maximize the signal. However, they should remain mutually exclusive in the pass band. The combined performance of absorbance (i.e., putting the two filters in series) is preferably not less than OD 4 throughout the range of interest.

The probe source and detector assembly functions as follows. Light from the LED 40" first passes through the short-pass filter 61 which cleans up the unwanted tail emission. The filtered light is then reflected forward by the dichroic mirror 47 (with higher wavelengths which escaped filtering passing through the mirror instead of being reflected). The reflected light is then focused by lens 65 onto fiber 46. Fiber 46 forwards the light to the splitter/coupler 53 which then passes onto the probe 30.

Light reflected by or fluorescing from a fluid sample is carried by the probe 30 and fiber 50 back to the splitter/coupler 53. The splitter/coupler 53 forwards a portion of the light via fiber 49 to the reflectance detector 42 and another portion (preferably 90% or more) to fiber 46. Light received by fiber 46 travels through the lens 65, and reaches the dichroic mirror 47. Because the fluorescence wavelengths are longer (i.e., they have undergone a red shift) than the reflected signal's wavelength, the fluorescence signal passes through the dichroic mirror, while the reflected light is again reflected by the dichroic mirror (toward the LED). The passed fluorescence signal is then received by the long-pass filter 63 and is converged onto the sensing area of fluorescence detector 44, which may be a photodiode. The long-pass filter 63 blocks the source scattering from entering the detector 44.

It should be noted that some color glass filters fluoresce. This means that while absorbing source scattering, the filter itself becomes a source of longer wavelengths. Thus, in accord with the preferred embodiment of the invention, a low fluorescent long-pass filter is utilized, or (as shown in FIG. 3) a dichroic long-pass filter is used in front of the color glass 65. Dichroic filters do not fluoresce.

As will be appreciated by those skilled in the art, the fluorescence yield of crude oils is a function of the excitation wavelength. Generally, fluorescence yield increases as the excitation wavelength decreases. Furthermore, the high fluorescence yield in the shorter wavelengths of excitation is accompanied by a stronger absorbance in crude oils. Therefore, the fluorescence signal intensity per unit source power increases as the source color moves from red to blue. For a strong fluorescence signal, it is desirable to use a blue source. However, using a red source has its advantages. When oil passes through the probe, it often leaves a thin oil residue on the tip. Depending on the wettability of the probe, oil films can have a significant effect on the signal. They cause an unstable water signal level and sometimes even a false positive of the oil detection. These problems are aggravated with the blue source and dark oils due to the strong absorbance and high fluorescence yield. Using a red excitation minimizes these problems, because both factors decrease for a given oil film thickness. But the low oil film effect is at the price of a lower signal. For light crudes, oil films do not cause a problem; rather, the weak signal is the main concern. In short, the preferred color of the source excitation depends on the crude oil to be measured. If desired, the apparatus of the invention may be equipped with more than one LED/color of excitation, e.g., NSPB500S, a Nichia blue LED (peak wavelength 470 nm); NSPG500S, a Nichia green LED (peak wavelength 520 nm), a TLRH180P, a red LED made by Toshiba (peak 644 nm; a secondary emission peak at 870 nm). Other LEDs having other excitation wavelengths may also be incorporated into the apparatus.

With the provided apparatus, the method of the invention for measuring oil velocity is carried out as seen in FIG. 5. At 100, a fluorescent quencher is injected into the continuous oil phase of the fluid stream downhole (upstream) of an optical probe, and a timer is started. At 102, the fluorescence of the oil is detected at the optical probe and monitored over time for a decrease (quenching) of the signal. If desired, the timer may be stopped when the (inverse) peak signal is obtained. The detected signal (or timer indication) and the distance between the location of injection and the location of detection are then used at 104 to calculate oil velocity; i.e., fluid velocity is determined by dividing the distance between the quencher ejection point and the optical probe position by the time it took the quencher to move that distance.

Fluorescence quenching may be accomplished in three fundamental ways: the tracer can absorb the source (excitation) light making it unavailable to excite fluorescence in the oil; the tracer may quench fluorescence of the crude oil by deactivating electronically excited states of the crude oil aromatic molecules which are primarily responsible for crude oil fluorescence; and the tracer can absorb fluorescing light thereby reducing the amount of light at the fluorescence wavelengths detected.

The first method, reduction of crude oil fluorescence by absorption of excitation light requires that the crude oil—quencher mixture be significantly darker than just the crude oil itself. This is easy to accomplish only for the lightly colored crude oils. For dark crude oils, this is difficult to accomplish at desirable concentrations of tracer ($\sim 10^{-3}$ to $10^{-4}$ per volume).

The second method of fluorescence reduction occurs by interaction of the electronically excited crude oil molecules (after photoabsorption) with the quencher. This interaction can occur via many different physics interactions such as resonant dipole coupling, spin-orbit coupling with paramagnetic tracers, adjacent heavy atom effect, chemical complex formation and chemical reaction.

It should be appreciated by those skilled in the art that a single quencher can reduce fluorescence both by absorption of source light and by quenching via one or more of the mechanisms listed here. In addition, recognizing that different mechanisms for quenching exist, various fluorescence quenchers or combinations thereof may be utilized. The quencher is preferably a liquid, and may take the form of a solute dissolved in a solvent. Thus, a solid quencher with one fluorescence reduction or quenching method can be dissolved in a liquid that reduces fluorescence by a second method.

Set forth below are some combination quenchers along with their fluorescence reduction values. The values are determined using the Stern-Volmer relation. The quenching measurement is determined by comparing the intensity of fluorescence from quenched ($I_F$) and unquenched ($I_{Fo}$) solutions as a function of quencher volume fraction <Q>.

Normally, molarity is used in the Stern-Volmer equation, but according to the invention, it is desirable to obtain maximum quenching for minimum tracer volume fraction. The Stern-Volmer equation is derived from the decay rate equation.

$$k_F = k_{Fo} + k_Q <Q> \quad (3)$$

where $k_F$ is the excited state decay rate, $k_{Fo}$ is the excited state decay rate in the absence of quencher Q and $k_Q$ is the quencher decay rate. Dividing by $k_{Fo}$ and noting that $k_F/k_{Fo} = I_{Fo}/I_F$, equation (3) leads to the Stern-Volmer equation.

$$(I_{Fo}/I_F) - 1 = k_Q/K_{Fo} <Q> \quad (4)$$

By plotting $I_{Fo}/I_F$ vs $<Q>$, one gets the quenching efficiency E $(=k_Q/k_{Fo})$. Table 1 lists the efficiency in crude oil of various systems for Q measured in volume fraction for excitation at 350 nm.

TABLE 1

Fluorescence reduction efficiencies for various solutions.

| Solute | Solvent | E |
|---|---|---|
| $CH_2I_2$ | Toluene | 180 |
| $CI_4$ | $CH_2I_2$ | 1700 |
| Eu Tris* | Toluene | 3.6 |
| (none) | $CH_2I_2$ | 280 |
| VO OEP | $CH_2I_2$ | 280 |

Eu Tris-Europium tris*(2,2,6,6-tetramethyl-3,5-heptanedionate)
VO OEP-Vanadyl Octaethylporphyrin The solutions in Table 1 were saturated in the solutes. The low solubility of certain solutes such as Eu Tris reduces the desirability of using those solutes in oil field applications in spite of their ability to quench. $CI_4$ is a very efficient quencher as is the adjacent heavy atom quencher $CH_2I_2$ (diiodomethane). The fact that diiodomethane is a liquid allows a high concentration of quencher per unit volume yielding a high quenching efficiency in Table 1. A solution of $CI_4$ in $CH_2I_2$ when present in crude oil in a concentration of $10^{-4}$ (i.e., 100 ppm) reduces crude oil fluorescence by 15%, which is easily measurable. However, such a solution is not preferred in the oil field because of the reactive chemistry of $CI_4$.

One of the best solvents known for crude oils, carbon disulfide (CS2), exhibits a strong quenching effect via quantum mechanical wave function mixing. Carbon tetrachloride (CCl4) quenches crude oil fluorescence via the solvent heavy atom effect that induces spin-orbit coupling in the excited fluorophores of crude oil. FIGS. 5a–5c show the effect on crude oil fluorescence of adding 1% CS2, 10% CS2, 1% CCl4 and 10% CCl4 to light, medium (API 29) and heavy (API 25) black oils. If there were no quenching effect, the act of dilution would increase crude oil fluorescence, although a 1% dilution would have a very small effect. However, quenching is significant and a 1% addition of quenchers has an easily measured effect.

Other quenchers may be used, such as high spin compounds with heavy atoms in peripheral positions, charge transfer complexes and Forster exchange complexes. Temperature may also be considered due to the fluorescence quenching that occurs in crude oils at elevated temperatures.

There have been described and illustrated herein several embodiments of apparatus and methods of measuring the velocity of flowing oil via the utilization of fluorescence quenchers. While particular embodiments of the invention have been described, it is not intended that the invention be limited thereto, as it is intended that the invention be as broad in scope as the art will allow and that the specification be read likewise. Thus, while the invention was described with reference to a particular wellbore tool, it will be appreciated that other wellbore tools could be utilized. As a result, rather than coupling the probes and/or the injector to bow springs, they may be coupled to mechanical arms, mounted to the body of the tool, coupled to bow springs, or placed into the flow stream with other means. Also, while the use of wellbore tools was described, the invention may be carried out through use of stationary apparatus and/or plumbing in or around the wellbore and may be cemented into place, provided quencher can be delivered to the flow stream, and provided that optics are located in the flow stream to detect fluorescence. In addition, while certain fluorescence quenching chemicals and chemical combinations were disclosed, it will be appreciated that other chemicals or combinations can be utilized. Further, while certain optical apparatus were disclosed for delivering light to the oil sample and for detecting the resulting fluorescence, it will be appreciated that different apparatus can be utilized. In fact, while a reflectance detector was shown, no such detector is required to carry out the invention. Likewise, while certain methods of finding oil velocity from the detected signal and from the distance between the injector and probe, it will be appreciated that other methods of analyzing the quenched signal could be utilized to find the oil velocity. Furthermore, while the invention was described with reference to finding oil velocity, it will be appreciated by those skilled in the art (and particularly with reference to the previously incorporated patents), that other parameters related to the oil may be obtained from the oil velocity information. Thus, the invention is not intended to be limited to simply finding oil velocity. It will therefore be appreciated by those skilled in the art that yet other modifications could be made to the provided invention without deviating from its spirit and scope as claimed.

We claim:

1. An apparatus for investigating a fluid stream containing oil, comprising:
    a) an injector which injects an oil fluorescence quenching marker into the oil of the fluid stream at a first location;
    b) a light source which subjects the fluid stream to light at a wavelength which will cause the oil in the fluid stream to naturally fluoresce;
    c) a fluorescence detection apparatus which detects at a second location a fluorescence signal from the oil in the fluid stream flowing past said second location.

2. An apparatus according to claim 1, wherein:
    said quenching marker is chosen from at least one of Europium tris*(2,2,6,6-tetramethyl-3,5-heptanedionate), $CH_2I_2$, $CI_4$, $CS_2$, and $CCl_4$.

3. An apparatus according to claim 1, wherein:
    said quenching marker is a solute dissolved in a solvent.

4. An apparatus according to claim 3, wherein:
    at least one of said solute and said solvent deactivates electronically excited states of aromatic molecules in the oil.

5. An apparatus according to claim 3, wherein:
    at least one of said solute and said solvent absorbs said light at said wavelength from said light source.

6. An apparatus according to claim 1, further comprising:
    d) a processor coupled to said fluorescence detection apparatus, said processor determining a velocity of the oil.

7. An apparatus according to claim 6, wherein:

said injector injects said oil fluorescence quenching marker at a first time, said fluorescence detection apparatus detects said fluorescence signal over a period of time including a second time after said first time, said second time including a peak in said fluorescence signal indicative of arrival of said oil fluorescence quenching marker, and said processor determines said velocity by dividing a distance between said first location and said second location by a difference in time from said first time to said second time.

8. An apparatus according to claim 1, wherein:

the oil is flowing in a well having a diameter "D", and said first location and said second location are separated by a distance d which is greater than 10D.

9. An apparatus according to claim 8, wherein:

said distance d is less than 100D.

10. An apparatus according to claim 1, wherein:

said fluorescence detection apparatus comprises an optical probe arranged in the fluid stream, a fiber optic coupled to the probe, an optical filter coupled to said fiber optic, and a fluorescence detector coupled to said optical filter.

11. An apparatus according to claim 10, wherein:

said fluorescence detection apparatus comprises a plurality of optical probes arranged in the fluid stream.

12. An apparatus according to claim 1, wherein said fluid stream is in a well, and wherein:

said injector is located on a logging tool suspended in the well.

13. An apparatus according to claim 12, wherein:

said fluorescence detection apparatus includes an optical probe arranged in the fluid stream and coupled to said logging tool.

14. An apparatus according to claim 12, wherein:

said logging tool includes a spring bow, and said fluorescence detection apparatus includes a plurality of optical probes arranged in the fluid stream and coupled to said spring bow.

15. An apparatus according to claim 12, wherein:

said light source is coupled to said logging tool.

16. A method for investigating a fluid stream containing oil, comprising:

a) injecting at a first time an oil fluorescence quenching marker into the oil of the fluid stream at a first location;

b) subjecting the fluid stream to light at a wavelength which will cause the oil in the fluid stream to naturally fluoresce;

c) detecting over a period of time at a second location a fluorescence signal from the oil in the fluid stream flowing past said detector, said period of time including a second time when the fluorescence of the oil in the fluid stream is at least partially quenched by said quenching marker.

17. A method according to claim 16, further comprising:

d) determining a velocity of the oil as a function of said first time, said second time, said first location and said second location.

18. A method according to claim 16, wherein:

said quenching marker is chosen from at least one of Europium tris*(2,2,6,6-tetramethyl-3,5-heptanedionate), $CH_2I_2$, $CI_4$, $CS_2$, and $CCl_4$.

19. A method according to claim 16, wherein:

said quenching marker is a solute dissolved in a solvent.

20. A method according to claim 19, wherein:

at least one of said solute and said solvent deactivates electronically excited states of aromatic molecules in the oil.

21. A method according to claim 19, wherein:

at least one of said solute and said solvent absorbs said light at said wavelength.

* * * * *